United States Patent [19]

Maas

[11] Patent Number: 4,598,281

[45] Date of Patent: Jul. 1, 1986

[54] ELECTRICAL LINE INTERRUPTION DETECTION AND ALARM CIRCUIT

[75] Inventor: Michael Maas, Uttenreuth, Fed. Rep. of Germany

[73] Assignee: Siemens Aktiengesellschaft, Berlin and Munich, Fed. Rep. of Germany

[21] Appl. No.: 557,519

[22] Filed: Dec. 2, 1983

[30] Foreign Application Priority Data

Dec. 15, 1982 [DE] Fed. Rep. of Germany ....... 3246473

[51] Int. Cl.$^4$ .............................................. G08B 21/00
[52] U.S. Cl. .................................... 340/664; 128/696; 128/731; 128/902; 128/908
[58] Field of Search ............... 340/664, 663, 661, 652, 340/651, 650, 649; 324/51; 307/355, 358, 359, 362; 128/696, 731, 734, 902, 908

[56] References Cited

U.S. PATENT DOCUMENTS

| | | | |
|---|---|---|---|
| 3,495,584 | 2/1970 | Schwalm | 128/696 |
| 3,559,193 | 1/1971 | Savaglio et al. | 128/908 X |
| 3,580,243 | 5/1971 | Johnson | 128/902 X |
| 3,602,215 | 8/1971 | Parnell | 128/696 |
| 3,732,859 | 5/1973 | Tateno | 128/731 |
| 3,905,364 | 9/1975 | Cudahy et al. | 128/696 |
| 4,092,981 | 6/1978 | Ertl | 128/731 |
| 4,141,351 | 2/1979 | James et al. | 128/696 |
| 4,191,195 | 3/1980 | Miller | 128/696 |
| 4,321,932 | 3/1982 | Francis | 128/696 |
| 4,488,110 | 12/1984 | Shirey et al. | 340/661 X |

Primary Examiner—James L. Rowland
Assistant Examiner—Daniel Myer
Attorney, Agent, or Firm—Mark H. Jay

[57] ABSTRACT

A circuit for detecting and indicating an interruption in the electrical connection between a signal device and a signal processing device, which has been provided with an amplifier at its input. The signal device has a relatively low impedance and the signal processing device has a relatively high impedance. The circuit includes an alarm device which generates an alarm when the predetermined upper limit of the amplifier input voltage has been exceeded. Also included are a supply circuit to feed an auxiliary dc current into the connection between the signal device and the signal processing device. The supplied auxiliary current is controlled by the amplifier input voltage to rise during an increased amplifier input voltage. As a result, a lower current supply can be provided under normal circumstances, which reduces misinterpretations. Preferably, the circuit is used in connection with ECG measuring devices.

14 Claims, 4 Drawing Figures

ELECTRICAL LINE INTERRUPTION DETECTION AND ALARM CIRCUIT

BACKGROUND OF THE INVENTION

The invention relates to an alarm circuit designed to detect interruptions in the electrical connection between a low impedance signal device and a signal processing device. The signal processing device has been provided with an amplifier at its input which has a higher input impedance than the impedance of the signal device as well as with a supply circuit to supply an auxiliary dc current to the connection between the signal device and the signal processing device. An alarm is activated as soon as a predetermined upper limit of the amplifier input voltage has been exceeded.

There are no restrictions with respect to the design of either the signal device or the signal processing device, as long as the above prerequisites are observed with respect to the input impedance of the respective devices. The signal device must have a comparatively low impedance and the signal processing device a comparatively higher impedance. For example, a microphone can be used as the signal device, while a microphone amplifier may be used as a signal processing device. However, the circuit is preferably used with a system applied to sense electrical voltages generated by a patient. Configurations of this kind are ECG, EEG and EMG devices. During the sensing of electrical voltages generated by the body of a patient, an electrical amplifier is attached to the patient via one or several electrodes and electrode lines. The satisfactory operation of a circuit of this type depends essentially on the existence of a proper connection between a patient and an amplifier input. As soon as the electrical circuit between the signal device (electrode) and the signal processing device (evaluation device with or without screen) is interrupted, reliable sensing of voltages generated by the patient is no longer ensured. As a result, signals measured during this time period may be misinterpreted. Therefore, prior art circuits include means to detect and indicate interruptions in the electrical input circuit of the amplifier.

Known circuits used in ECG measurements monitor the upper limits of the source impedance (patient circuit), which is connected to the amplifier input. Under normal conditions the source impedance lies below the upper limit. The source impedance is comprised of the impedance of the supply lines between the electrode and the signal processing device as well as the tissue impedance and the electrode transfer impedance. During interruptions, such as may occur when an electrode is removed from the patient, the impedance value exceeds the predetermined upper limit. The alarm device interprets this increase as in impedance a line interruption.

In prior art devices, the source impedance is monitored by feeding an electrical current of approximately constant amplitude into the input of the amplifier which comprises the connection point between the signal device and the signal processing device. The voltage measured at the input of the amplifier can then be used to determine the magnitude of the source impedance and an alarm will be generated when a predeterminable limit is exceeded. In order not to distort the signals that are sensed from the patient, which range between 0.1 Hz to 1 kHz frequency, prior art devices employ a signal with a frequency far exceeding this range. For this purpose, a dc signal (Siemens brochure "System SIRECUST 400" E 3331, order number M-E 331/2077, article number 73 70 059 E 2254) or an ac signal of around 12 kHz (Siemens brochure "System SIRECUST 400", E 331, order number M-E 331.2077, article number 73 70 000 E 2253) may be used. However, both alternatives present disadvantages as described below.

For example, when supplying an approximately constant auxiliary dc current, the following disadvantages occur:

(a) Changes in the source impedance may lead to an erroneous voltage, superimposed on the voltage to be sensed.

(b) A dc current supplied via the electrodes increases the polarization voltage at the electrodes, that is to say, the voltage flowing between the electrode metal (usually Ag/AgCL) and the electrode contact gel. In turn this polarization voltage can be modulated by movements of the patient.

Both effects (a) and (b) can create motion artefacts which interfere with the evaluation process and/or the screen display.

(c) The dc current changes the electrode surface. This means, that the surface is more readily prone to build-ups or modifications (chemical changes) of the metal used for the electrode. This is certainly true for Ag/AgCl which is commonly used.

(d) The dc current leads to ion migration through the skin of the patient. It also changes the chemical composition within the tissue and the contact electrolytes usually located between the skin and the electrode surface.

The severity of the adverse effects mentioned above are increased in proportion to the magnitude of the applied auxiliary dc current. Therefore, it is recommended that low current values be used. However, this current value is limited to a certain minimum due to the insulation resistance of the total configuration and the amplitude of the source voltage to be processed. The type of insulation selected for the supply lines determines to a large degree the insulation resistance.

In order to prevent these disadvantages the alternate method mentioned above is used. An auxiliary ac current of relatively high frequency, e.g. 12 kHz is supplied. However, this approach has the disadvantage of an already low insulation impedance due to the line capacitance. Therefore only a relatively low impedance limit can be monitored as source impedance. In addition, the ac current feed-in can lead to interruptions during the presence of high frequency interference voltages. High frequency interference voltages might occur for example in connection with high frequency surgery.

SUMMARY OF THE INVENTION

It is the objective of this invention to provide a circuit arrangement with dc current supply, which considerably reduces the above mentioned disadvantages. Insofar as the signal processing device is a voltage sensing device, the signal to noise ratio of the useful signal provided by the signal device is greater than 1.

According to the present invention, this objective has been met by the previously mentioned circuit arrangement. The auxiliary dc current is controlled in the supply circuit by the amplifier input voltage. This produces the effect of a rising auxiliary dc current with increasing amplifier input voltage.

Therefore, this circuit arrangement also monitors the source impedance by means of an auxiliary dc current. However, in contrast to the previously described prior art circuit arrangements, the auxiliary dc current does not have an approximately constant amplitude. Instead, the auxiliary dc current changes automatically with the voltage present at the input of the amplifier. That is to say, the higher the input voltage, the high the applied auxiliary dc current.

A circuit arrangement of this kind has been selected, because in a majority of instances the input voltage of the amplifier is much lower than the maximum voltage to be processed, that is the voltage sensed from a patient. Under normal conditions, it is therefore possible to use a lower current value for line monitoring purposes. At the same time, less adverse effects are generated by the lower auxiliary dc current. That is to say, fewer interference signals are generated due to movements by the patient. Only under certain conditions, such as shortly before the involuntary removal of an electrode, is an auxiliary dc current similar to those applied with known circuit arrangements supplied.

According to the preferred embodiment, the auxiliary dc current is derived from the output voltage of the amplifier or generated by means of an electrical resistor, for example.

Other features and advantages of the invention will be apparent from the following description of the preferred embodiments, and from the claims.

For a full understanding of the present invention, reference should now be made to the following detailed description of the preferred embodiments of the invention and to the accompanying drawings.

DETAILED DESCRIPTION

Figure 1:
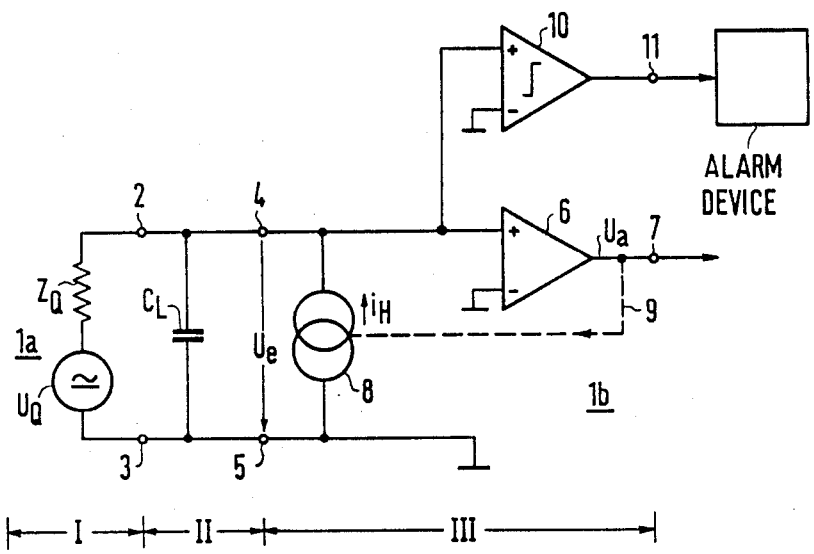
FIG. 1 shows the basic configuration of a circuit arrangement according to the invention to detect line interruptions.

The basic circuit according to FIG. 1 relates to the voltages to be sensed from the patient. Toward this end, three regions I, II and III are defined. The first region I includes one or several electrodes and the patient, represented as signal device 1a. The source impedance, which is generated by the electrode to skin transfer resistance (resistance between the electrode and the skin), has been identified with $Z_Q$. Source impedance $Z_Q$ is of relative low impedance. The source voltage, that is to say the voltage generated by the electrodes, has been identified with $U_Q$. The output terminals of signal device 1a have been identified by reference numerals 2 and 3. The second region II includes the supply line between signal device 1a and the signal processing device 1b located to the right in the drawing. This supply line is identified by the line capacitance $C_L$ between the supply lines.

Input voltage $U_e$ is present at the input terminals 4, 5, of signal processing device 1b. Input terminal 4 is connected to one (positive) signal input of amplifier 6, while input terminal 5 is connected to a reference potential. The other (negative) signal input of amplifier 6 is also connected to the reference potential. Signal processing device 1b has a relatively high input impedance between input terminals 4, 5. The increased signal voltage or output voltage present at the output terminal 7 of amplifier 6 has been identified with $U_a$. Output voltage $U_a$ is processed by signal processing device 1b to be used in the conventional manner for automatic evaluations or for screen display. The third region III, which extends between input terminals 4, 5 and output terminal 7, includes amplifier 6 of device 1b and a circuit arrangement designed for line monitoring.

According to FIG. 1, an auxiliary dc current $i_H$ is introduced between input terminals 4, 5. This process is depicted by the connection of an auxiliary current source 8. The supplied auxiliary dc current $i_H$ is used to monitor source impedance $Z_Q$. As shown by dotted line 9, the supplied auxiliary dc current $i_H$ is controlled by the amplifier output voltage $U_a$ and therefore by the amplifier input voltage $U_e$. Control is automatic. During increasing amplifier input voltage $U_e$, auxiliary dc current $i_H$ rises and vice versa. Therefore, depicted elements 8, 9 designate a supply circuit.

Alarm device 10 is included in region III. Alarm device 10 is a threshold switch to discern excessive source impedances. One (positive) signal input is connected to the amplifier input voltage $U_e$, while the other (negative) signal input is connected to the reference potential. The upper limit of alarm device 10 is defined as $U_{e2}$. If $U_{e2}$ is exceeded by the amplifier input voltage $U_e$, an alarm message is generated at output 11 of the alarm device, activating the alarm.

Figure 2:
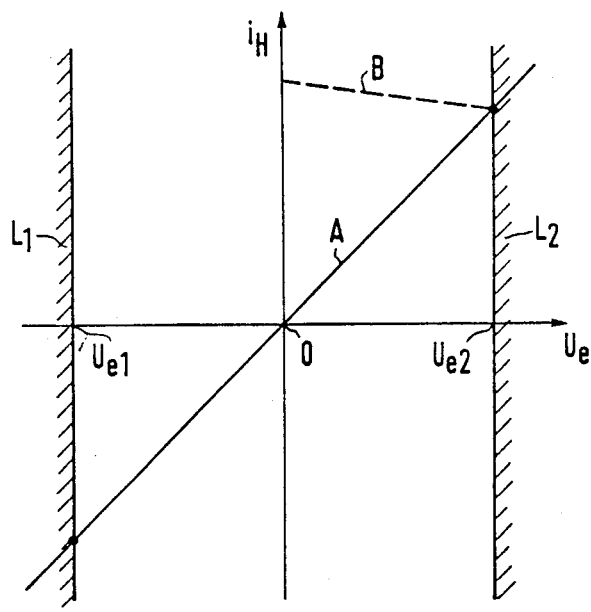
FIG. 2 shows a preferred, linear circuit-voltage characteristic for an auxiliary dc current supply.

Alarm device 10 can be of conventional design. As can be seen in FIG. 2, in addition to the upper limit $U_{e2}$, alarm device 10 can also include a lower voltage limit $U_{e1}$. As with the upper limit, an alarm will be generated if the input voltage $U_e$ is smaller than the lower voltage limit.

FIG. 2 shows a preferred characteristic for the auxiliary dc current supply included in a circuit arrangement designed for detecting line interruptions. In FIG. 2, characteristic A designates the dependence of auxiliary dc current $i_H$ on input voltage $U_e$ of amplifier 6. Characteristic A is a straight line. It extends between the negative and the positive values of input voltage $U_e$ and travels linearly through point 0 volts. FIG. 2 also depicts upper limit $U_{e2}$ and lower limit $U_{e1}$ of alarm device 10. Should either limit be exceeded, alarm device 10 will generate an alarm message. Both alarm ranges are depicted as shaded areas. The upper alarm range is identified with $L_2$, the lower with $L_1$. In this manner voltage monitoring is provided, which reacts to the positive upper as well as to the negative lower limit values $U_{e2}$ and $U_{e1}$, respectively.

FIG. 2 also includes a straight dashed line characteristic B. Characteristic B identifies a conventional auxiliary current supply mode by means of a high impedance resistor. In contrast to the present invention, the auxiliary dc current $i_H$ remains essentially constant in known circuit arrangements. Furthermore, it even decreases slightly with higher input voltages $U_e$.

Figure 3:
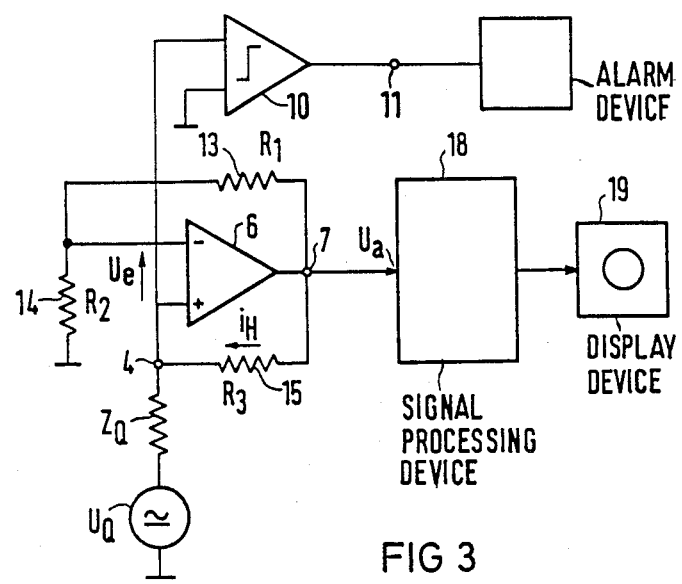
FIG. 3 shows an especially simple circuit implementation of the circuit according to the invention.

FIG. 3 shows a very simple embodiment of amplifier 6 with variable auxiliary dc current supply. At the positive signal input 4 of amplifier 6, source impedance $Z_Q$ is connected in series with source voltage $U_Q$. The negative signal input is connected to output 7 via a first feedback resistor (resistor in the feedback path) $R_1$ (13)

and to the reference potential via a second feedback resistor $R_2$ (14). In addition, a supply resistor $R_3$ (15) is located between output 7 and the positive signal input 4 of amplifier 6. With this embodiment, the auxiliary dc current $i_H$ flowing through input resistor 15 is derived from output voltage $U_a$ of amplifier 6.

The values of resistors 13, 14, 15 are such, that either the upper (positive) or the lower (negative) limit of amplifier 6 is reached, as soon as the source impedance $Z_Q$ exceeds a predetermined value. In both cases an alarm will be generated. This can be also expressed as follows: If the ratio of the resistor values $R_1$, $R_2$ of feedback resistors 13 and 14 exceed the ratio of the resistor value $R_3$ to the source impedance $Z_Q$, i.e.

$$R_1/R_2 > R_3/Z_Q$$

the alarm will be activated.

FIG. 3 also shows that the amplifier output voltage is forwarded to signal processing device 18. Device 18 supplies a signal display device 19. It can display the evaluated signal, e.g. the ECG or EEG, of the patient. If required, the signal can also be displayed graphically.

As can be seen from FIG. 3, amplifier 6 is a feedback amplifier, whereby the source resistor $Z_Q$ affects the amplification factor. With the previously mentioned upper limit of the source impedance $Z_Q$, the loop amplification barely exceeds +1, and the output voltage $U_a$ of amplifier 6 extends into the positive or negative limit. This means, that the output voltage $U_a$ reached the limit determined by resistors 13, 14, 15. At that time, the supplied auxiliary dc current $i_H$ has increased to such a degree, that the input voltage $U_e$ reaches a value, which lies above or below the established limits $U_{e2}$, $U_{e1}$ of the alarm device 10.

In order to evaluate the advantages which are offered by the circuit arrangement shown in FIG. 3, the following comparison is made: An input voltage $U_e$ range of $+/-1$ volts is to be processed without error (alarm) messages. The dc voltage, present during normal operations, that is to say with Ag/AgCl-electrodes and sensed from the patient, is in the range of $+/-10$ mV. In comparison to conventional dc supplies with the same triggering value for the source impedance (an alarm is generated with this triggering value), the present circuit arrangement supplies an auxiliary dc current $i_H$, which requires only 1/100 of the amplitude necessary with prior art devices. As a result, the present arrangement is less sensitive to patient movements.

Figure 4:
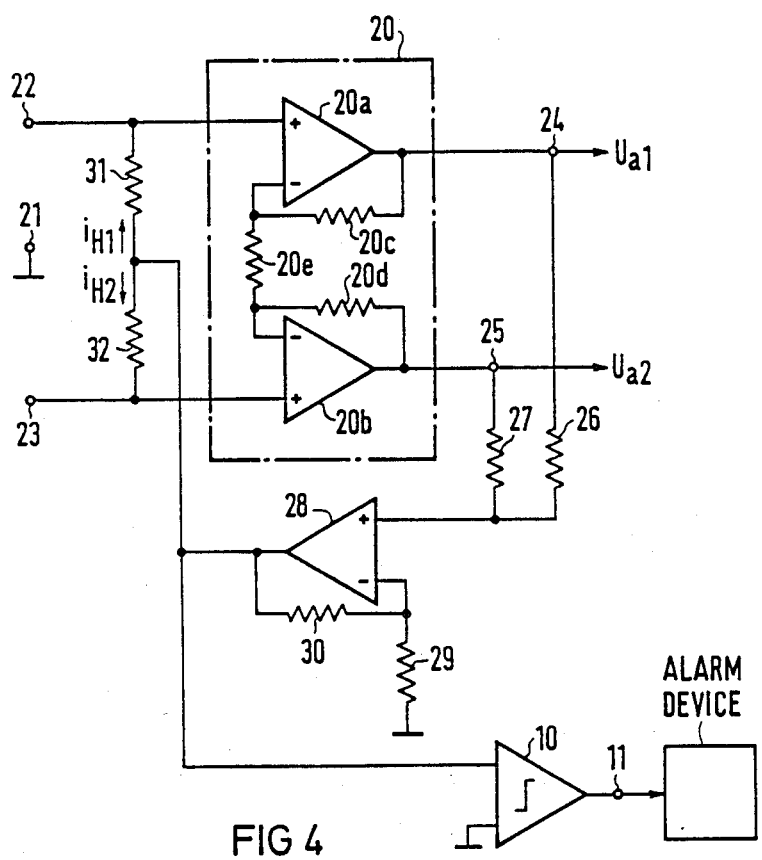
FIG. 4 shows a circuit arrangement according to the invention, whereby the auxiliary dc current is fed into a two-stage differential amplifier via a positive feedback circuit.

FIG. 4 shows a circuit arrangement, which includes three electrodes (not shown), preferably three ECG electrodes to sense voltages generated by a patient. In this embodiment, the amplifier is designed as differential amplifier 20 with symmetrical inputs. Differential amplifier 20 consists of two single amplifiers 20a and 20b, which are designed as operational amplifiers. Via the so-called neutral electrode, the patient is connected at first output 21 to the reference potential of differential amplifier 20. The second electrode is connected to second input 22 and the third electrode to third input 23. Second input 22 is connected with the (positive) signal input of single amplifier 20a and the third input 23 with the positive input of single amplifier 20b. Inputs 22, 23 are the differential inputs of differential amplifier 20. Resistors 20c, 20d, and 20e are conventionally used. Amplified output signals can be tapped at outputs 24, 25 of single amplifiers 20a and 20b.

The circuit arrangement according to FIG. 4 monitors the three electrode connections. Two (auxiliary) dc currents $i_{H1}$ and $i_{H2}$ are supplied to both differential inputs 22 and 23. For this purpose, outputs 24 and 25 are connected to a resistor network, comprised of resistors 26 and 27 connected in series. These resistors 26 and 27 are used to provide the mean value of the output voltages $U_{a1}$, $U_{a2}$ at the outputs 24 and 25. This mean value is forwarded to a feedback amplifier 28, which operates simultaneously with the operational amplifier. Feedback amplifier 28 is therefore located in the feedback loop of both single amplifiers 20a, 20b. In addition, feedback amplifier 28 has a realtively high amplification factor, e.g. 3.7. The resistors of feedback amplifier 28 have been identified with 29 and 30. The output signal of feedback amplifier is split into two auxiliary dc currents $i_{H1}$ and $i_{H2}$. These currents are forwarded to inputs 22 and 23 of single amplifiers 20a and 20b via the high impedance supply resistors 31 and 32. The impedance supply resistors 31, 32 may be of 100 MOhm value.

As can be seen from the embodiment shown in FIG. 4, one single supply circuit 26 to 32 is applied to both single amplifiers 20a and 20b.

According to the present embodiment, the comparator or alarm device 10 is connected to the output of feedback amplifier 28. This concept offers two advantages. A low impedance signal is present at the output and only one comparator 10 is required. Alarm device 10, which could be described as a window comparator (window discriminator), also includes two limiting values and generates an alarm at its output 11 as soon as one of these limits has been exceeded. However, as an alternative solution, an individual alarm device or comparator (not shown) could be connected to outputs 24 and 25. In this case, each comparator would have to respond to both limiting values. But a configuration of this kind would require additional expenditures.

As can be seen, the above embodiment used the same principle. By means of a circuit, auxiliary dc currents $i_{H1}$, $i_{H2}$ are derived from the output voltage, in this case from the mean value of output voltages $U_{a1}$, $U_{a2}$.

To prevent self-oscillations, known circuit components (compensation networks) should be used in connection with the circuit arrangement according to FIG. 4.

With the circuit arrangement according to FIG. 4, an alarm will be generated as soon as one of the three electrodes is no longer present at inputs 21, 22, 23. This is achieved in part by the previously mentioned relatively high amplification of feedback amplifier 28.

There has thus been shown and described novel apparatus for line interruption detection which fulfills all the objects and advantages sought therefor. Many changes, modifications, variations and other uses and applications of the subject invention will, however, become apparent to those skilled in the art after considering this specification and the accompanying drawings which disclose preferred embodiments thereof. All such changes, modifications, variations and other uses and applications which do not depart from the spirit and scope of the invention are deemed to be covered by the invention which is limited only by the claims which follow.

What is claimed is:

1. A circuit for detecting excessive impedances between a body under test and an input of a signal processing device which contains an amplifier, said signal processing device being connected to said body by a low impedance electrical connection, and said input having a voltage applied thereto by said connection comprising:

(a) a supply circuit to supply a variable auxiliary DC current to said electrical connection, said circuit operating to increase said current with increasing voltage at said input; and (b) an alarm device which generates an alarm indicating excessive impedance when said input voltage is outside a predetermined range.

2. The circuit of claim 1, wherein said supply circuit derives said auxiliary DC current from an output voltage of said amplifier.

3. The circuit as recited in claim 2, wherein said amplifier is an operational amplifier and wherein an ohmic feedback resistor is provided between the output of said operational amplifier and said electrical connection, said feedback resistor being operative for generating said auxiliary DC current.

4. The circuit as recited in claim 3, wherein said feedback resistor has a high impedance in comparison to the impedance of said signal processing device.

5. The circuit as recited in claim 2, further comprising a feedback amplifier, said feedback amplifier being connected between the output of said amplifier and the input of said signal processing device.

6. The circuit as recited in claim 2, wherein said supply circuit operates such that said auxiliary DC current is linearly related to said input voltage of said signal processing device.

7. The circuit as recited in claim 1, further comprising a feedback amplifier, said feedback amplifier being connected between the output of said amplifier and the input of said signal processing device.

8. The circuit as recited in claim 1, wherein said supply circuit is connected for supplying an auxiliary DC current to a multiplicity of electrical connections formed between signal devices and said signal processing device, and wherein said alarm is responsive to an excessive impedance in any of said signal devices.

9. The circuit as recited in claim 8, wherein said supply circuit comprises at least one differential amplifier, said differential amplifier being operative for handling three signal devices; and wherein a resistor network is employed for connecting the outputs of said differential amplifier to the inputs of said differential amplifier, said resistor network generating a mean voltage reference.

10. The circuit as recited in claim 1, wherein said signal device is a voltage sensing electrode for connection to a patient.

11. The circuit as recited in claim 10, wherein said voltage sensing electrode is an ECG electrode.

12. The circuit as recited in claim 1, wherein said supply circuit operates such that auxiliary DC current is linearly related to said input voltage of said signal processing device.

13. The circuit as recited in claim 1, wherein said alarm device operates in a manner that said alarm is generated when said input voltage is below a lower limit of said range.

14. The circuit as recited in claim 1, wherein said alarm device operates in a manner that said alarm is generated when said input voltage is above an upper limit of said range.

* * * * *